United States Patent [19]

Meier

[11] Patent Number: 4,759,862
[45] Date of Patent: Jul. 26, 1988

[54] O,P-BIFUNCTIONALIZED O'-SUBSTITUTED PHENOLS

[75] Inventor: Hans R. Meier, Marly, Switzerland

[73] Assignee: Ciba-Geigy Corporation, Ardsley, N.Y.

[21] Appl. No.: 80,149

[22] Filed: Jul. 30, 1987

Related U.S. Application Data

[63] Continuation of Ser. No. 741,389, Jun. 5, 1985, abandoned.

[30] Foreign Application Priority Data

Jun. 12, 1984 [CH] Switzerland .......................... 2835/84

[51] Int. Cl.$^4$ ................... C10M 135/30; C01C 149/32
[52] U.S. Cl. ..................................... 252/47.5; 252/47; 252/48.6; 568/55
[58] Field of Search ................. 568/55; 252/47.5, 48.6, 252/47

[56] References Cited

U.S. PATENT DOCUMENTS

| | | | |
|---|---|---|---|
| 3,227,677 | 1/1966 | Simpson | 568/55 |
| 3,660,352 | 5/1972 | Song | 568/55 |
| 3,903,173 | 9/1975 | Eggensperger et al. | 568/55 |
| 4,091,037 | 5/1978 | Arold | 568/55 |
| 4,358,616 | 11/1982 | Wedemeyer et al. | 568/55 |

FOREIGN PATENT DOCUMENTS 1569743  6/1969  France .................................. 568/55
1206262  9/1970  United Kingdom ................. 568/55

OTHER PUBLICATIONS

Chemical Abstracts, 97, 41279u, (1982).
Chem. Abstracts Service Registry Handbook, 1965–1971, No. 15479-46-6.

Primary Examiner—Richard L. Raymond
Assistant Examiner—Raymond Covington
Attorney, Agent, or Firm—Luther A. R. Hall

[57] ABSTRACT

Novel bifunctionalized o-substituted phenols of the formula I

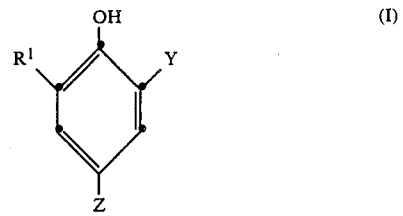

are described. Reference should be made to the description in respect of the meaning of the substituents $R^1$, Y and Z.

The novel substances are suitable as stabilizers for organic polymers and for mineral oils or synthetic oils.

14 Claims, No Drawings

O,P-BIFUNCTIONALIZED O'-SUBSTITUTED PHENOLS

This is a continuation of application Ser. No. 741,389, filed on June 5, 1985, now abandoned.

The present invention relates to novel bifunctionalised phenols, compositions containing these compounds and a method of stabilising organic material using these substances.

Bifunctionalised thiomethyl-containing phenols are known. U.S. Pat. No. 4,091,037 describes a process for the preparation of alkylthiomethylphenols, 2,4-bis-(ethylthiomethyl)-phenol being mentioned specifically.

The use of 2,4,6-trialkyl-bis-(3,5-alkylthiomethyl)-phenols as antioxidants in polymers is proposed in U.S. Pat. No. 3,660,352. Finally, U.S. Pat. No. 3,227,677 describes, inter alia, 2,6-bis-(alkoxycarbonylalkylenethiomethyl)-4-alkylphenols as stabilisers for polyolefines.

According to British Patent Specification No. 1,184,533, 2,4-bis-(alkylthiomethyl)-3,6-dialkylphenols can be used as stabilisers for organic polymers and for synthetic oils.

The invention relates to compounds of the formula I

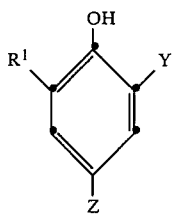

in which $R^1$ is $C_2$–$C_{20}$-alkyl, $C_3$–$C_{20}$-alkenylmethyl, $C_3$–$C_{20}$-alkinylmethyl, $C_5$–$C_{12}$-cycloalkyl, phenyl, 1- or 2-naphthyl, $C_7$–$C_{14}$-alkaryl or $C_7$–$C_{14}$-aralkyl, Y is $-CH_2-S-R^2$ and Z is $-CH_2-S-R^3$, or in which Y and/or Z is a radical

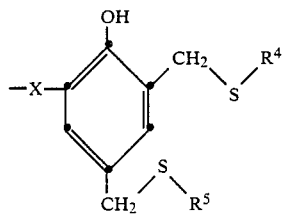

in which $R^2$, $R^3$, $R^4$ and $R^5$ independently of one another are $C_1$–$C_{20}$-alkyl, $C_2$–$C_{20}$-alkyl which is substituted by a phenyl radical and/or one or two hydroxyl groups, $C_3$–$C_{20}$-alkenylmethyl, $C_3$–$C_{20}$-alkinylmethyl, $C_5$–$C_{12}$-cycloalkyl, phenyl, 1- or 2-naphthyl, $C_7$–$C_{14}$-alkaryl, $C_7$–$C_{14}$-aralkyl, $C_5$–$C_7$-cycloalkyl which is substituted by hydroxyl in the 2-position, or 1,3-benzothiazol-2-yl, or radicals of the formulae $-C(R^6R^7)-(CHR^8)_m-W$, $-(CH_2)_2-OCO-R^{15}$ or

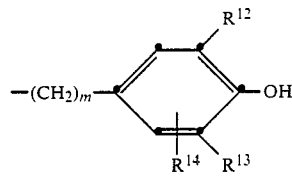

in which m is 0, 1 or 2, $R^6$, $R^7$ and $R^8$ independently of one another are hydrogen or $C_1$–$C_6$-alkyl, W is a radical $-COR^9$, $-CN$, $-COOR^{10}$ or $-CON(R^{10}R^{11})$, in which $R^9$ is hydrogen, $C_1$–$C_{20}$-alkyl, phenyl, 1- or 2-naphthyl, $C_5$–$C_{12}$-cycloalkyl, $C_7$–$C_{14}$-aralkyl or $C_7$–$C_{14}$-alkaryl and in which $R^{10}$ and $R^{11}$ independently of one another have the meanings of $R^9$, or are additionally $C_2$–$C_{20}$-alkyl which is substituted by a hydroxyl or cyano group, or are $C_3$–$C_{20}$-alkyl which is interrupted by one to five $-O-$, $-S-$, $-N(CH_3)-$ or $-N(C_2H_5)-$ and is unsubstituted or substituted by a hydroxyl group, it being necessary for the several heteroatoms which may occur to be separated by at least one methylene group, in which $R^{10}$ or $R^{11}$ is $C_2$–$C_{12}$-alkenyl, $C_2$–$C_{12}$-alkinyl, phenyl which is substituted by one or two $-NO_2$, $-Cl$, $-Br$, $-OCH_3$ or $-COOR^{18}$, or a group

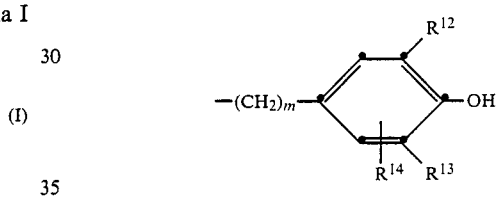

or in which $R^{10}$ and $R^{11}$, together with the nitrogen atom, form a five-, six- or seven-membered heterocyclic ring, which may also contain a further heteroatom, in which $R^{12}$, $R^{13}$ and $R^{14}$ independently of one another are hydrogen, $C_1$–$C_{20}$-alkyl, cyclohexyl or phenyl, in which $R^{15}$ is $C_1$–$C_{20}$-alkyl, $C_5$–$C_{12}$-cycloalkyl, $C_7$–$C_{14}$-aralkyl, $C_7$–$C_{14}$-alkaryl, phenyl, 1- or 2-naphthyl or a radical

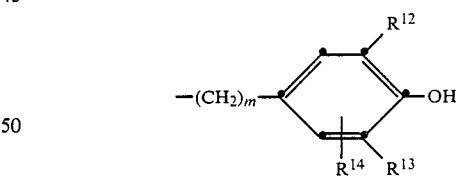

in which X is $-C(R^{16}R^{17})-$, $-S-$ or $-S-S-$, in which $R^{16}$ and $R^{17}$ independently of one another are hydrogen, $C_1$–$C_6$-alkyl, cyclohexyl or phenyl, and in which, finally, $R^{18}$ is $C_1$–$C_6$-alkyl, cyclohexyl, phenyl, benzyl or tolyl.

Compounds of the formula I in which Y is $-CH_2-S-R^2$ and Z is $-CH_2-S-R^3$ are preferred.

Compounds of the formula I which are also of interest are those in which Y is $-CH_2-S-R^2$ and Z is $-CH_2-S-R^3$, in which $R^1$ is branched $C_3$–$C_{12}$-alkyl, $C_5$–$C_9$-cycloalkyl, phenyl or $C_7$–$C_9$-aralkyl, in which $R^2$ and $R^3$ independently of one another are $C_4$–$C_{14}$-alkyl, $C_2$–$C_{14}$-alkyl which is substituted by a phenyl and/or one or two hydroxyl groups, allyl, propargyl, $C_5$–$C_9$-cycloalkyl, 2-hydroxycyclohexyl, phenyl, 1,3- benzothiazol-2-yl or $C_7$–$C_9$-aralkyl, or are a radical —$C(R^6R^7)$—$(CHR^8)_m$—W, —$(CH_2)_2$—OCO—$R^{15}$ or

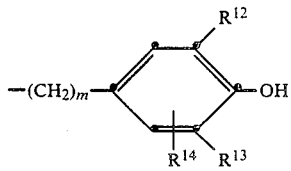

in which m is 0, 1 or 2, and in which $R^6$, $R^7$ and $R^8$ independently of one another are hydrogen or methyl, W is —$COOR^{10}$ or —$CON(R^{10}R^{11})$, in which $R^{10}$ and $R^{11}$ independently of one another are hydrogen, $C_1$–$C_{12}$-alkyl, phenyl, $C_5$–$C_9$-cycloalkyl, $C_7$–$C_9$-aralkyl, 2-hydroxyethyl, 2-cyanoethyl, or $C_3$–$C_{12}$-alkyl which is interrupted by one to three —O— and is unsubstituted or substituted by a hydroxyl group, it being necessary for several oxygen atoms which may occur to be separated by at least one methylene group, in which $R^{10}$ and $R^{11}$ are allyl, propargyl, phenyl which is substituted by a —Cl, —$COOCH_3$ or —$OCH_3$, or a radical

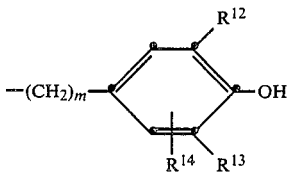

or in which $R^{10}$ and $R^{11}$, together with the common nitrogen atom, form a pyrrole, piperidine, pyrrolidine, hexamethyleneimine or morpholine ring, in which $R^{12}$, $R^{13}$ and $R^{14}$ independently of one another are hydrogen or $C_1$–$C_{12}$-alkyl, and in which $R^{15}$ is $C_1$–$C_{12}$-alkyl, $C_5$–$C_9$-cycloalkyl, $C_7$–$C_9$-aralkyl, phenyl or a radical

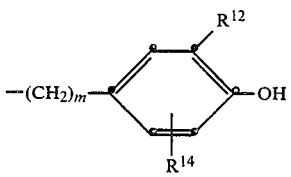

Particularly preferred compounds of the formula I are those in which Y is —$CH_2$—S—$R^2$ and Z is —$CH_2$—S—$R^3$, in which $R^1$ is tert.-butyl, cyclohexyl, phenyl or benzyl, in which $R^2$ and $R^3$ independently of one another are $C_4$–$C_{14}$-alkyl, 2-hydroxyethyl, 2,3-dihydroxypropyl, 1-phenyl-2-hydroxyethyl, cyclohexyl, phenyl, benzyl or a radical —$(CH_2)_{m+1}$—W, in which W is —$COOR^{10}$ or —$CON(R^{10}R^{11})$, m is 0, 1 or 2, and in which, finally, $R^{10}$ and $R^{11}$ independently of one another are hydrogen, $C_1$–$C_{12}$-alkyl, phenyl, cyclohexyl, benzyl, 2-hydroxyethyl, 2-hydroxypropyl, 3-oxabutyl or —$(CH_2$—$CH_2$—$O)_n$—$CH_2$—$CH_2$—OH, in which n is 1, 2 or 3, or in which $R^{10}$ and $R^{11}$ are

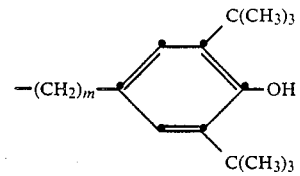

or, together with the common nitrogen atom, form a piperidine or morpholine ring.

Compounds of the formula I which are also preferred are those in which Y is —$CH_2$—S—$R^2$ and Z is —$CH_2$—S—$R^3$, $R^1$ is tert.-butyl, cyclohexyl, phenyl or benzyl, and in which $R^2$ and $R^3$ independently of one another are $C_4$–$C_{14}$-alkyl, 2-hydroxyethyl, 2,3-dihydroxypropyl, 1-phenyl-2-hydroxyethyl, cyclohexyl, phenyl or benzyl.

Compounds of the formula I which are also preferred are those in which Y is —$CH_2$—S—$R^2$ and Z is —$CH_2$—S—$R^3$, $R^1$ is tert.-butyl, cyclohexyl, phenyl or benzyl, in which $R^2$ and $R^3$ are radicals of the formula —$(CH_2)_{m+1}$—W, in which W is —$COOR^{10}$ or —$CON(R^{10}R^{11})$, and in which $R^{10}$ and $R^{11}$ independently of one another denote hydrogen, $C_1$–$C_{12}$-alkyl, phenyl, cyclohexyl, benzyl, 2-hydroxyethyl, 2-hydroxypropyl, 5-hydroxy-3-oxapentyl or 3-oxabutyl, or are a radical

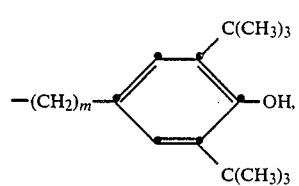

or in which $R^{10}$ and $R^{11}$, together with the common nitrogen atom, form a piperidine or morpholine ring, and in which, finally, m is 0, 1 or 2.

Especially preferred compounds of the formula I are those in which Y is —$CH_2$—S—$R^2$ and in which Z is —$CH_2$—S—$R^3$, in which $R^1$ is tert.-butyl, phenyl, cyclohexyl or benzyl, in which $R^2$ and $R^3$ are radicals of the formula

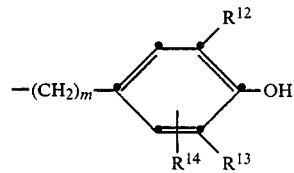

in which m is 0, 1 or 2, and in which, finally, $R^{12}$, $R^{13}$ and $R^{14}$ independently of one another are hydrogen or $C_1$–$C_{12}$-alkyl.

Particularly preferred compounds of the formula I are those in which Y is —$CH_2$—S—$R^2$ and Z is —$CH_2$—S—$R^3$, and in which $R^1$ is tert.-butyl and $R^2$ and $R^3$ independently of one another are $C_4$–$C_{14}$-alkyl.

Compounds of the formula I which are also of interest are those in which X is —$CH_2$—, —$CH(CH_3)$—, —$C(CH_3)_2$— or —S—.

A $C_2$–$C_{20}$-alkyl radical $R^1$ is, for example, ethyl, n-propyl, isopropyl, n-butyl, sec.-butyl, tert.-butyl, n-pentyl, isopentyl, n-hexyl, 1,1-dimethylbutyl, n-heptyl, n-octyl, 2-ethylhexyl, n-nonyl, n-decyl, 1,1,3,3-tetramethylbutyl, 1,1,3,3-tetramethylhexyl, n-undecyl, n-dodecyl, 1,1,3,3,5,5-hexamethylhexyl, n-tetradecyl, n-hexadecyl, n-octadecyl or n-eicosyl.

$R^1$ is particularly preferably $C_4$–$C_{20}$-alkyl, and is then, for example, n-butyl, sec.-butyl, tert.-butyl, n-pentyl, isopentyl, n-hexyl, 1,1-dimethylbutyl, n-octyl, 2-ethylhexyl, n-decyl, 1,1,3,3-tetramethylbutyl, n-dodecyl, 1,1,3,3,5,5-hexamethylhexyl, n-tetradedyl, n-hexadecyl, n-octadecyl or n-eicosyl.

$R^1$ is particularly preferably branched $C_3$–$C_{12}$-alkyl and is then, for example, isopropyl, sec.-butyl, tert.-butyl, isopentyl, 2-ethylhexyl, 1,1-dimethylbutyl, 1,1,3,3-tetramethylbutyl, 1,1,3,3-tetramethylhexyl or 1,1,3,3,5,5-hexamethylhexyl. A tert.-butyl radical $R^1$ is of particular interest.

A $C_1$–$C_{20}$-alkyl radical $R^2$, $R^3$, $R^4$, $R^5$, $R^9$, $R^{10}$, $R^{11}$, $R^{12}$, $R^{13}$, $R^{14}$ or $R^{15}$ is also methyl, in addition to the radicals mentioned as examples for $R^1$.

$R^2$, $R^3$, $R^4$ and $R^5$ are preferably $C_4$–$C_{14}$-alkyl, and then denote, for example, n-butyl, sec.-butyl, tert.-butyl, n-pentyl, isopentyl, n-hexyl, n-heptyl, n-octyl, 2-ethylhexyl, 1,1,3,3-tetramethylbutyl (called t-octyl below), n-nonyl, n-decyl, n-dodecyl, 1,1,3,3,5,5-hexamethylhexyl, 2,2,4,6,6-pentamethylhept-4-yl (called t-dodecyl below) or n-tetradecyl.

$R^2$, $R^3$, $R^4$ and $R^5$ are especially preferably $C_8$–$C_{14}$-alkyl, and in particular n-octyl, 2-ethylhexyl, t-octyl, n-dodecyl or t-dodecyl.

$R^9$, $R^{10}$, $R^{11}$, $R^{12}$, $R^{13}$, $R^{14}$ and $R^{15}$ are preferably $C_1$–$C_{12}$-alkyl, and are then, for example, methyl, ethyl, n-propyl, isopropyl, n-butyl, sec.-butyl, tert.-butyl, n-pentyl, isopentyl, n-hexyl, n-heptyl, n-octyl, 2-ethylhexyl, n-nonyl, n-decyl or n-dodecyl.

A $C_1$–$C_6$-alkyl radical $R^6$, $R^7$, $R^8$, $R^{16}$, $R^{17}$ or $R^{18}$ is, for example, methyl, ethyl, n-propyl, isopropyl, n-butyl, sec.-butyl, tert.-butyl, n-pentyl, isopentyl or n-hexyl.

$R^6$, $R^7$, $R^8$, $R^{16}$, $R^{17}$ and $R^{18}$ are preferably straight-chain $C_1$–$C_6$-alkyl radicals, and particularly preferably methyl.

A $C_3$–$C_{20}$-alkenylmethyl radical $R^1$, $R^2$, $R^3$, $R^4$ or $R^5$ is, for example, allyl, isopropenyl, oct-7-enyl, dodec-11-enyl, oleyl or octadec-17-enyl. Allyl is preferred.

A $C_2$–$C_{12}$-alkenyl radical $R^{10}$ or $R^{11}$ is, for example, vinyl, allyl, but-3-enyl, pent-4-enyl, hex-5-enyl, oct-7-enyl, dec-9-enyl or dodec-11-enyl. Vinyl or allyl is preferred. If $R^1$, $R^2$, $R^3$, $R^4$ or $R^5$ is $C_3$–$C_{20}$-alkinylmethyl, this is, for example, propargyl, but-3-inyl, hex-5-inyl, oct-7-inyl, dec-9-inyl, dodec-11-inyl, tetradec-13-inyl, hexadec-15-inyl, octadec-17-inyl or eicos-19-inyl. Propargyl is preferred.

A $C_2$–$C_{12}$-alkinyl radical $R^{10}$ or $R^{11}$ is, for example, ethinyl, propargyl, but-3-inyl, hex-5-inyl, oct-7-inyl, dec-9-inyl or dodec-11-inyl. Propargyl is preferred.

A $C_5$–$C_{12}$-cycloalkyl radical $R^1$, $R^2$, $R^3$, $R^4$, $R^5$, $R^9$, $R^{10}$, $R^{11}$ or $R^{15}$ is, for example, cyclopentyl, cyclohexyl, cycloheptyl, cyclooctyl, cyclononyl, cyclodecyl, cycloundecyl or cyclododecyl. These radicals are preferably $C_5$–$C_9$-cycloalkyl, and in particular cyclohexyl.

A $C_7$–$C_{14}$-aralkyl radical $R^1$, $R^2$, $R^3$, $R^4$, $R^5$, $R^9$, $R^{10}$, $R^{11}$ or $R^{15}$ is, for example, benzyl, phenethyl, α-methylbenzyl, α,α-dimethylbenzyl, phenylbutyl, phenyl-α,α-dimethylpropyl, phenylhexyl, phenyl-α,α-dimethylbutyl, phenyloctyl or phenyl-α,α-dimethylhexyl. Benzyl is preferred.

A $C_7$–$C_{14}$-alkaryl radical $R^1$, $R^2$, $R^3$, $R^4$, $R^5$, $R^9$, $R^{10}$, $R^{11}$ and $R^{15}$ is, for example o-, m- or p-tolyl, 2,3-, 2,4-, 2,5-, 2,6-, 3,4- or 3,5-dimethylphenyl, o-, m- or p-ethylphenyl, o-, m- or p-propylphenyl, o-, m- or p-isopropylphenyl, o-, m- or p-butylphenyl, o-, m- or p-sec.-butylphenyl, o-, m- or p-tert.-butylphenyl, 2,3-, 2,4-, 2,5-, 2,6-, 3,4-, 3,5- or 3,6-dibutylphenyl or -di-tert.-butylphenyl or o-, m- or p-hexylphenyl or o-, m- or p-octylphenyl. o-, m- or p-Tolyl is preferred.

A $C_2$–$C_{20}$-alkyl radical $R^2$, $R^3$, $R^4$ or $R^5$ which is substituted by a phenyl radical and/or one or two hydroxyl groups is, for example, 2-hydroxyethyl, 2-hydroxypropyl, 2-hydroxybutyl, 2-hydroxyhexyl, 2-hydroxyoctyl, 2-hydroxydecyl, 2-hydroxydodecyl, 2-hydroxytetradecyl, 2-hydroxyhexadecyl, 2-hydroxyoctadecyl, 2-hydroxyeicosyl, 1-phenyl-2-hydroxyethyl, 1-phenyl-2-hydroxypropyl, 1-phenyl-2-hydroxybutyl, 1-phenyl-2-hydroxyethyl, 1-phenyl-2-hydroxyoctyl, 1-phenyl-2-hydroxydecyl, 1-phenyl-2-hydroxydodecyl, 1-phenyl-2-hydroxytetradecyl, 1-phenyl-2-hydroxyhexadecyl, 1-phenyl-2-hydroxyoctadecyl, 1-phenyl-2-hydroxyeicosyl or 2,3-dihydroxypropyl. $C_2$–$C_{14}$-Alkyl which is substituted by a phenyl radical and/or one or two hydroxyl groups is preferred. 2-Hydroxyethyl, 2-hydroxypropyl, 2,3-dihydroxypropyl or 1-phenyl-2-hydroxyethyl is especially preferred.

A $C_5$–$C_7$-cycloalkyl radical $R^2$, $R^3$, $R^4$ or $R^5$ which is substituted in the 2-position by hydroxyl is, for example, 2-hydroxycyclopentyl, 2-hydroxycyclohexyl or 2-hydroxycycloheptyl. 2-Hydroxycyclohexyl is particularly preferred.

A $C_2$–$C_{20}$-alkyl radical $R^{10}$ or $R^{11}$ which is substituted by a hydroxyl or cyano group is, for example, 2-hydroxyethyl, 2-hydroxypropyl, 2-hydroxybutyl, 2-hydroxyhexyl, 2-hydroxyoctyl, 2-hydroxydecyl, 2-hydroxydodecyl, 2-hydroxytetradecyl, 2-hydroxyhexadecyl, 2-hydroxyoctadecyl, 2-hydroxyeicosyl or 2-cyanoethyl. 2-Hydroxyethyl, 2-hydroxypropyl or 2-cyanoethyl is preferred.

A $C_3$–$C_{20}$-alkyl radical $R^{10}$ or $R^{11}$ which is interrupted by one to five —O—, —S—, —N(CH$_3$)— or —N(C$_2$H$_5$)— and is unsubstituted or substituted by a hydroxyl group is, for example, 3-oxabutyl, 3,6-dioxaheptyl, 3,6,9-trioxadecyl, 3,6,9,12-tetraoxatridecyl, 3,6,9,12,15-pentaoxahexadecyl, 3,6,9,12,15,18-hexaoxanonadecyl, 5-hydroxy-3-oxapentyl, 8-hydroxy-3,6-dioxaoctyl, 11-hydroxy-3,6,9-trioxaundecyl, 14-hydroxy-3,6,9,12-tetraoxatetradecyl, 3-thiabutyl, 5-hydroxy-3-azamethylpentyl, 5-hydroxy-3-azaethylpentyl, 3-azamethyl-6-oxaheptyl, 3-azaethyl-6-oxaheptyl, 3-azamethylbutyl or 3-azaethylbutyl.

$C_3$–$C_{12}$-Alkyl radicals which are interrupted by —O— and are unsubstituted or substituted by a hydroxyl group are preferred. 5-Hydroxy-3-oxapentyl or 3-oxabutyl is especially preferred.

A phenyl radical $R^{10}$ or $R^{11}$ which is substituted by one or two —NO$_2$, —Cl, —Br, —OCH$_3$ or —COOR$^{18}$ is, for example, o-, m- or p-nitrophenyl, -chlorophenyl, -bromophenyl, -methoxyphenyl, -methoxycarbonylphenyl or -ethoxycarbonylphenyl, or 2,3-, 2,4-, 2,5-, 2,6-, 3,4- or 3,5-dinitrophenyl, -dichlorophenyl, -dibromophenyl, -dimethoxyphenyl, -dimethoxycarbonylphenyl or -diethoxycarbonylphenyl.

o-, m- or p-Chlorophenyl, -methoxyphenyl or -methoxycarbonylphenyl is preferred. If $R^{10}$ and $R^{11}$, together with the common nitrogen atom, form a five-, six- or seven-membered heterocyclic ring which may also contain a further heteroatom, this ring is, for example, pyrrole, 2-H-pyrrole, imidazole, pyrazole, hexamethyleneimine, pyrrolidine, pyrroline, imidazolidine, imidazoline, pyrazolidine, pyrazoline, piperidine, piperazine or morpholine. Pyrrole, pyrrolidine, piperidine or morpholine is preferred, and piperidine or morpholine is especially preferred.

X is preferably —C($R^{16}R^{17}$)— or —S—, and particularly preferably —C($R^{16}R^{17}$)—. $R^{16}$ and $R^{17}$ are preferably hydrogen or $C_1$-$C_6$-alkyl. Especially preferred radicals X are —$CH_2$—, —CH($CH_3$)— and —C($CH_3$)$_2$—.

The substances listed below may be regarded as examples of representatives of compounds of the formula I: 2,4-bis(methylthiomethyl)-6-tert.-butylphenol, 2,4-bis-(ethylthiomethyl)-6-tert.-butylphenol, 2,4-bis-(n-propylthiomethyl)-6-tert.-butylphenol, 2,4-bis-(n-butylthiomethyl)-6-tert.-butylphenol, 2,4-bis-(n-hexylthiomethyl)-6-tert.-butylphenol, 2,4-bis-(n-octylthiomethyl)-6-tert.-butylphenol, 2,4-bis-(n-decylthiomethyl)-6-tert.-butylphenol, 2,4-bis-(n-dodecylthiomethyl)-6-tert.-butylphenol, 2,4-bis-(n-tetradecylthiomethyl)-6-tert.-butylphenol, 2,4-bis-(n-hexadecylthiomethyl)-6-tert.-butylphenol, 2,4-bis-(n-octadecylthiomethyl)-6-tert.-butylphenol, 2,4-bis-(n-eicosylthiomethyl)-6-tert.-butylphenol, 2,4-bis-(isopropylthiomethyl)-6-tert.-butylphenol, 2,4-bis-(sec-butylthiomethyl)-6-tert.-butylphenol, 2,4-bis-(tert.-butylthiomethyl)-6-tert.-butylphenol, 2,4-bis-(2-ethylhexylthiomethyl)-6-tert.-butylphenol, 2,4-bis-(1,1,3,3-tetramethylbutylthiomethyl)-6-tert.-butylphenol, 2,4-bis-(1,1,3,3,5,5-hexamethylhexylthiomethyl)-6-tert.-butylphenol, 2,4-bis-(n-octylthiomethyl)-6-isopropylphenol, 2,4-bis-(n-dodecylthiomethyl)-6-isopropylphenol, 2,4-bis-(n-octylthiomethyl)-6-(2-ethylhexyl)-phenol, 2,4-bis-(n-dodecylthiomethyl)-6-(2-ethylhexyl)-phenol, 2,4-bis-[4-(2,2,4,6,6-pentamethylheptyl)-thiomethyl]-6-tert.-butylphenol, 2,4-bis-(n-octylthiomethyl)-6-(1,1-dimethylbutyl)-phenol, 2,4-bis-(n-dodecylthiomethyl)-6-(1,1-dimethylbutyl)-phenol, 2,4-bis-(n-dodecylthiomethyl)-6-(1,1-dimethylpropyl)-phenol, 2,4-bis-(n-octylthiomethyl)-6-cyclohexylphenol, 2,4-bis-(n-dodecylthiomethyl)-6-cyclohexylphenol, 2,4-bis-(n-octylthiomethyl)-6-phenylphenol, 2,4-bis-(n-dodecylthiomethyl)-6-phenylphenol, 2,4-bis-(n-octylthiomethyl)-6-benzylphenol, 2,4-bis-(n-dodecylthiomethyl)-6-benzylphenol, 2,4-bis-(n-dodecylthiomethyl)-6-(α,α-dimethylbenzyl)-phenol, 2,4-bis-(n-octylthiomethyl)-6-p-tolylphenol, 2,4-bis-(n-dodecylthiomethyl)-6-p-tolylphenol, 2,4-bis-(n-octylthiomethyl)-6-prop-2-enylphenol, 2,4-bis-(n-dodecylthiomethyl)-6-prop-2-enylphenol, 2,4-bis-(n-dodecylthiomethyl)-6-prop-2-inylphenol, 2,4-bis-(prop-2-enylthiomethyl)-6-tert.-butylphenol, 2,4-bis-(prop-2-inylthiomethyl)-6-tert.-butylphenol, 2,4-bis-(cyclohexylthiomethyl)-6-tert.-butylphenol, 2,4-bis-(2-hydroxycyclohexylthiomethyl)-6-tert.-butylphenol, 2,4-bis-(phenylthiomethyl)-6-tert.-butylphenol, 2,4-bis-(benzylthiomethyl)-6-tert.-butylphenol, 2,4-bis-(p-tolylthiomethyl)-6-tert.-butylphenol, the dimethyl ester of 2,4-bis-(3-carboxy-2-thiapropyl)-6-tert.-butylphenol, 2,4-bis-(3-carboxy-2-thiapropyl)-6-tert.-butylphenol, the dibutyl ester of 2,4-bis-(3-carboxy-2-thiapropyl)-6-tert.-butylphenol, the dioctyl ester of 2,4-bis-(3-carboxy-2-thiapropyl)-6-tert.-butylphenol, the didodecyl ester of 2,4-bis-(3-carboxy-2-thiapropyl)-6-tert.-butylphenol, the monomethyl ester of 2,4-bis-(3-carboxy-2-thiapropyl)-6-tert.-butylphenol, the dimethyl ester of 2,4-bis-(4-carboxy-2-thiabutyl)-6-tert.-butylphenol, the dioctyl ester of 2,4-bis-(4-carboxy-2-thiabutyl)-6-tert.-butylphenol, the di-(2-ethylhexyl) ester of 2,4-bis-(3-carboxy-2-thiapropyl)-6-tert.-butylphenol, the dimethyl ester of 2,4-bis-(3-carboxy-2-thiabutyl)-6-tert.-butylphenol, the dimethyl ester of 2,4-bis-(4-carboxy-3-methyl-2-thiapentyl)-6-tert.-butylphenol, the N,N-dimethylamide of 2,4-bis-(3-carboxy-2-thiapropyl)-6-tert.-butylphenol, the N,N-dihexylamide of 2,4-bis-(3-carboxy-2-thiapropyl)-6-tert.-butylphenol, the N,N-didodecylamide of 2,4-bis-(3-carboxy-2-thiapropyl)-6-tert.-butylphenol, the N,N-dimethylamide of 2,4-bis-(4-carboxy-2-thiabutyl)-6-tert.-butylphenol, the N,N-dimethylamide of 2,4-bis-[3-carboxy-2-thiabutyl]-6-tert.-butylphenol, the N,N-dibutylamide of 2,4-bis-(4-carboxy-3-methyl-2-thiapentyl)-6-tert.-butylphenol, the dicyclohexyl ester of 2,4-bis-(3-carboxy-2-thiapropyl)-6-tert.-butylphenol, the diphenyl ester of 2,4-bis-(3-carboxy-2-thiapropyl)-6-tert.-butylphenol, the dibenzyl ester of 2,4-bis-(3-carboxy-2-thiapropyl)-6-tert.-butylphenol, the di-p-tolyl ester of 2,4-bis-(3-carboxy-2-thiapropyl)-6-tert.-butylphenol, the di-(3-thiabutyl) ester of 2,4-bis-(3-carboxy-2-thiapropyl)-6-tert.-butylphenol, the di-(3-oxabutyl) ester of 2,4-bis-(3-carboxy-2-thiapropyl)-6-tert.-butylphenol, the di-(N,N-dimethylamino-2-ethyl) ester of 2,4-bis-(3-carboxy-2-thiapropyl)-6-tert.-butylphenol, the diamide of 2,4-bis-(3-carboxy-2-thiapropyl)-6-tert.-butylphenol, the diamide of 2,4-bis-(4-carboxy-2-thiabutyl)-6-tert.-butylphenol, 2,4-bis-(prop-2-enylthiomethyl)-6-tert.-butylphenol, 2,4-bis-(prop-2-inylthiomethyl)-6-tert.-butylphenol, 2,4-bis-[2-hydroxyethylthiomethyl]-6-tert.-butylphenol, 2,4-bis-[2-cyanoethylthiomethyl]-6-tert.-butylphenol, 2,4-bis-[(4-methoxyphenyl)-thiomethyl]-6-tert.-butylphenol, 2,4-bis-[(4-chlorophenyl)-thiomethyl]-6-tert.-butylphenol, 2,4-bis-[(2-methoxycarbonylphenyl)-thiomethyl]-6-tert.-butylphenol, 2,4-bis-[(1,3-benzthiazol-2-yl)-thiomethyl]-6-tert.-butylphenol, 2,4-bis-[2,3-dihydroxypropylthiomethyl]-6-tert.-butylphenol, 2,4-bis-[(3,5-di-tert.-butyl-4-hydroxyphenyl)thiomethyl]-6-tert.-butylphenol, 2,4-bis-[4-(3,5-di-tert.-butyl-4-hydroxyphenyl)-2-thiabutyl]-6-tert.-butylphenol, 2,4-bis-[4-acetoxy-2-thiabutyl]-6-tert.-butylphenol, 2,4-bis-[3-formyl-2-thiabutyl]-6-tert.-butylphenol and 2,4-bis-[3-acetyl-2-thiabutyl]-6-tert.-butylphenol.

The compounds of the formula I are prepared by processes which are known per se. Thus, for example, analogously to the description in British Patent Specification No. 1,184,533, one mole of a suitably o-substituted phenol or of a 2,2'-bisphenol is reacted with two or four moles of formaldehyde and the corresponding amounts of suitably substituted mercaptans. Mixtures of different mercaptans can also be used.

The reaction can be carried out in the presence or absence of an organic solvent and in the presence of a basic catalyst.

Suitable solvents are alcohols with one to six carbon atoms, for example methanol, ethanol, propanol, butanol, pentanol or hexanol. It is also possible to use diols, polyols and ethers thereof, such as glycol, glycerol or polyethylene glycol. The reaction can also be carried out in polar aprotic solvents, such as, for example, dimethylformamide or dimethylsulfoxide, or aromatic or aliphatic, chlorinated or non-chlorinated hydrocarbons, for example toluene, ligroin or chlorobenzene, can be employed. Basic catalysts which are used are, for example, organic bases, such as dialkylamines or trialkylamines, or inorganic bases are taken, such as hydroxides, preferably alkali metal hydroxides. However, inorganic bases are preferably only used if the reactants contain no hydrolysable groups, for example ester or amide groups.

Instead of formaldehyde, it is also possible to use compounds which form formaldehyde under the reaction conditions. These include, for example, paraformaldehyde and hexamethylenetetramine.

The reaction mixture is heated under reflux in a nitrogen atmosphere for 5 to 40 hours.

After cooling to room temperature, the organic phase is diluted with a suitable solvent, for example with toluene, chloroform, methylene chloride, ether or methyl isobutyl ketone. It is then washed neutral with aqueous acid. Acetic acid, for example, can be used for this, but it is also possible to take any other desired acid, for example a mineral acid.

After being separated off in the usual way, the organic phase is concentrated in vacuo and, if necessary, the evaporation residue is further purified, for example by recrystallisation, by column chromatography or by filtration over a short silica gel column.

The compounds of the formula I can, however, also be synthesised by a process analogous to that described in U.S. Pat. No. 4,091,037 by reacting a suitable Mannich base and at least the stoichiometric amount of a suitable mercaptan in the presence or absence of a suitable organic solvent under a nitrogen atmosphere. Mixtures of mercaptans can also be employed. The reaction temperature is between 100° C. and 160° C. The same organic solvents as for the variant described above are suitable. The reaction can be accelerated by applying a slight vacuum (0.1 to 0.6 bar). Working up is carried out as already described above.

In another variant of the preparation process for compounds of the formula I, suitably substituted chloromethylphenols are used as starting substances. These are reacted with at least the equivalent amount of mercaptan or mercaptide. If necessary, an amount of base equivalent to the mercaptan is added. The base can be added during or after the reaction. It serves to neutralise the hydrogen chloride liberated. Suitable bases are trialkylamines, pyridines, potassium carbonate and alkali metal or alkaline earth metal hydroxides.

The o-substituted phenols, chloromethylphenols or Mannic bases to be used as starting substances are known or can be prepared by known processes. Thus, 2,4-bis-(dialkylaminomethyl)-6-tert.-butylphenols are described in C.A. 97, 41279, whilst 2,4-bis-(chloromethyl)-6-methylphenols are referred to in C.A. 95, 669.

The invention furthermore relates to compositions containing an organic material which is sensitive towards thermal, oxidative or radiation-induced degradation and at least one compound of the formula I, preferably a compound of the formula I in which $R^1$ is tert.-butyl, cyclohexyl, phenyl or benzyl, Y is $-CH_2-S-R^2$, Z is $-CH_2-S-R^3$ and in which $R^2$ and $R^3$ independently of one another are $C_4-C_{14}$-alkyl, 2-hydroxyethyl, 2,3-dihydroxypropyl, phenyl or benzyl. Compositions containing the compounds of the formula I mentioned above as preferred, in which $R^2$ and $R^3$ independently of one another are $C_4-C_{14}$-alkyl are also of interest.

Compositions which are furthermore preferred contain an organic material which is sensitive towards thermal, oxidative or radiation-induced degradation and at least one compound of the formula I in which $R^1$ is tert.-butyl, cyclohexyl, phenyl or benzyl, in which Y is $-CH_2-S-R^2$ and Z is $-CH_2-S-R^3$, and in which $R^2$ and $R^3$ are $-(CH_2)_{m+1}-W$, in which m is 0, 1 or 2, and in which W is $-COOR^{10}$ or $-CON(R^{10}R^{11})$, in which $R^{10}$ and $R^{11}$ independently of one another are $C_1-C_{12}$-alkyl, phenyl, cyclohexyl, benzyl, or $C_3-C_{12}$-alkyl which is interrupted by $-O-$.

In a preferred embodiment, the compositions according to the invention contain mixtures of compounds of the formula I. Compositions in which the organic material is a polymer, in particular an elastomer, are furthermore preferred. Particularly preferred elastomers are the following:

Polydienes, such as, for example, polybutadiene, polyisoprene or polychloroprene; block polymers, for example styrene/butadiene/styrene, styrene/isoprene/styrene or styrene/ethylene-propylene/styrene types; and acrylonitrile/butadiene polymers.

These polymers can also be in the form of latices and can be stabilised as such.

Compositions in which the organic material is a synthetic lubricant or a lubricant based on mineral oil are also preferred.

Possible lubricants are familiar to the expert and are described, for example, in "Schmiermittel Taschenbuch (Pocketbook of Lubricants) (Hüthig Verlag, Heidelberg, 1974)".

The invention also relates to the use of compounds of the formula I as stabilisers for organic material against damage thereof by the effect of oxygen, heat, light and high-energy radiation.

The compounds are preferably used as antioxidants in organic polymers, in particular in elastomers, or as mineral oils or synthetic oils.

The compounds according to the invention are also suitable as EP/AW additives for lubricants or as additives for metalworking fluids.

Other examples of organic material which can advantageously be stabilised with the compounds according to the invention are:

1. Polymers of mono- and di-olefines, for example polyethylene (which may be crosslinked), polypropylene, polyisobutylene, polybut-1-ene, polymethylpent-1-ene, polyisoprene or polybutadiene, and polymers of cycloolefines, for example of cyclopentene or norbornene.

2. Mixtures of the polymers mentioned under (1), for example mixtures of polypropylene with polyisobutylene.

3. Copolymers of mono- and di-olefines with one another or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), and terpolymers of ethylene with propylene and a diene, such as hexadiene, dicyclopentadiene or ethylidenenorbornene.

4. Polystyrene and poly-(p-methylstyrene).

5. Copolymers of styrene or α-methylstyrene with dienes or acrylic derivatives, for example styrene/butadiene, styrene/acrylonitrile, styrene/alkyl methacrylate, styrene/maleic anhydride and styrene/acrylonitrile/methyl acrylate; high impact strength mixtures of styrene copolymers and another polymer, for example a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

6. Graft copolymers of styrene, for example styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under (5), such as are known, for example, as so-called ABS, MBS, ASA or AES polymers.

7. Halogen-containing polymers, for example polychloroprene, chlorinated rubber, chlorinated or chlorosulfonated polyethylene and epichlorohydrin homopolymers or copolymers, in particular polymers of halogen-containing vinyl compounds, for example polyvinyl chloride, polyvinylidene chloride and polyvinylidene fluoride; as well as copolymers thereof, such as vinyl chloride/vinylidene chloride, vinyl chloride/vinyl acetate or vinylidene chloride/vinyl acetate.

8. Polymers which are derived from α,β-unsaturated acids and derivatives thereof, such as polyacrylates and polymethacrylates, polyacrylamides and polyacrylonitriles.

9. Copolymers of the monomers mentioned under (8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers which are derived from unsaturated alcohols and amines or their acyl derivatives or acetals, such as polyvinyl alcohol, polyvinyl acetate, stearate, benzoate or maleate, polyvinylbutyral, polyallyl phthalate and polyallyl melamine.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene, and polyoxymethylenes containing comonomers, for example ethylene oxide.

13. Polyphenyl oxides and sulfides and mixtures thereof with styrene polymers.

14. Polyurethanes which are derived from polyethers, polyesters and polybutadienes with terminal hydroxyl groups on the one hand, and aliphatic or aromatic polyisocyanates on the other hand, and intermediates thereof.

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-m-phenylene-isophthalamide and block copolymers thereof with polyethers, for example with polyethylene glycol, polypropylene glycol or polytetramethylene glycol.

16. Polyureas, polyimides, polyamide-imides and polybenzimideazoles.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates, and block polyetheresters which are derived from polyethers with hydroxyl end groups.

18. Polycarbonates and polyester-carbonates.

19. Polysulfones, polyether-sulfones and polyetherketones.

20. Crosslinked polymers which are derived from aldehydes on the one hand and phenols, urea or melamine on the other hand, such as phenol/formaldehyde, urea/formaldehyde and melamine/formaldehyde resins.

21. Drying and non-drying alkyd resins.

22. Unsaturated polyester resins which are derived from copolyesters of saturated and unsaturated dicarboxylic acids with polyhydric alcohols, and vinyl compounds as crosslinking agents, and also their halogen-containing modifications which are difficult to ignite.

23. Crosslinkable acrylic resins which are derived from substituted acrylic acid esters, for example from epoxy-acrylates, urethane-acrylates or polyester-acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bis-glycidyl ethers or from cycloaliphatic diepoxides.

26. Naturally occurring polymers, such as cellulose, natural rubber, gelatine and polymer-homologously chemically modified derivatives thereof, such as cellulose acetates, propionates and butyrates, and the cellulose ethers, such as methylcellulose.

27. Mixtures (polyblends) of the abovementioned polymers, for example PP/EPDM, polyamide 6/EPDM or ABS, PVC/EVA, PVC/ABS, PVC/MBS, PC/ABS and PBTP/ABS.

28. Naturally occurring and synthetic organic substances which are pure monomeric compounds or mixtures thereof, for example mineral oils, animal or vegetable fats, oils and waxes, or oils, waxes and fats based on synthetic esters (for example phthalates, adipates, phosphates or trimellitates), and admixtures of synthetic esters with mineral oils in any desired weight ratios, such as are used, for example, as spinning preparations, and aqueous emulsions thereof.

29. Aqueous emulsions of natural or synthetic rubbers, for example natural rubber latex or latices of carboxylated styrene/butadiene copolymers.

The stabilisers are added to the plastics or the lubricants in a concentration of 0.01–10% by weight, based on the material to be stabilised. Preferably, 0.05 to 5.0% by weight, and particularly preferably 0.1 to 2.0% by weight, of the compounds, based on the material to be stabilised, is incorporated into these compounds.

Incorporation can be effected, for example, by mixing in the substances of the formula I and, if appropriate, other additives by methods which are customary in the art, before or during shaping, or by applying the dissolved or dispersed compounds to the polymer, if appropriate with subsequent evaporation of the solvent. The novel compounds can also be added in the form of a masterbatch containing these compounds, for example, in a concentration of 2.5 to 25% by weight to the plastic to be stabilised.

In the case of crosslinked polyethylene, the compounds are added before the crosslinking.

The materials stabilised in this way can be used in the most diverse forms, for example as films, fibres, tapes, moulding compositions or profiles, or as binders for lacquers, adhesives or putty.

The phenols of the formula I can be employed in practice together with other stabilisers.

Lubricant formulations can additionally also contain other additives, which are added to improve certain use properties, for example other aminic antioxidants, metal passivators, rust inhibitors, agents which improve the viscosity index, agents which reduce the pour point, dispersants/surfactants and wear protection additives.

Examples of other additives with which the stabilisers used according to the invention can be employed together are:

1. Antioxidants 1.1. Alkylated monophenols: 2,6-di-tert.-butyl-4-methylphenol, 2-tert.-butyl-4,6-dimethylphenol, 2,6-di-tert.-butyl-4-ethylphenol, 2,6-di-tert.-butyl-4-n-butylphenol, 2,6-di-tert.-butyl-4-i-butylphenol, 2,6-di-cyclopentyl-4-methylphenol, 2-(α-methylcyclohexyl)-4,6-dimethylphenol, 2,6-dioctadecyl-4-methylphenol, 2,4,6-tri-cyclohexylphenol and 2,6-di-tert.-butyl-4-methoxymethylphenol.

1.2. Alkylated hydroquinones: 2,6-di-tert.-butyl-4-methoxyphenol, 2,5-di-tert.-butyl-hydroquinone, 2,5-di-tert.-amylhydroquinone and 2,6-diphenyl-4-octadecyloxyphenol.

1.3. Hydroxylated thiodiphenyl ethers: 2,2'-thio-bis-(6-tert.-butyl-4-methylphenol), 2,2'-thio-bis-(4-octylphenol), 4,4'-thio-bis-(6-tert.-butyl-3-methylphenol) and 4,4'-thiobis-(6-tert.-butyl-2-methylphenol).

1.4. Alkylidene-bisphenols: 2,2'-methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.-butylphenol), 2,2'-ethylidene-bis-(4,6-di-tert.-butylphenol), 2,2'-ethylidene-bis-(6-tert.-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert.-butylphenol), 4,4'-methylene-bis-(6-tert.-butyl-2-methylphenol), 1,1-bis-(5-tert.-butyl-4-hydroxy-2-methylphenyl)butane, 2,6-di-(3-tert.-butyl-5-methyl-2-hydroxybenzyl)-4-methylphenol, 1,1,3-tris-(5-tert.-butyl-4-hydroxy-2-methylphenyl)-butane, 1,1-bis-(5-tert.-butyl-4-hydroxy-2-methylphenyl)-3-n-dodecyl-mercaptobutane, ethylene glycol bis-[3,3-bis-(3'-tert.-butyl-4'-hydroxyphenyl)-butyrate[, di-(3-tert.-butyl-4-hydroxy-5-methylphenyl)-dicyclopentadiene and di-]2-(3'-tert.-butyl-2'-hydroxy-5'-methyl-benzyl)-6-tert.-butyl-4-methyl-phenyl] terephthalate.

1.5. Benzyl compounds: 1,3,5-tri-(3,5-di-tert.-butyl-4-hydroxybenzyl)-2,4,6-trimethylbenzene, di-(3,5-di-tert.-butyl-4-hydroxybenzyl) sulfide, isooctyl 3,5-di-tert.-butyl-4-hydroxybenzyl-mercaptoacetate, bis-(4-tert.-butyl-3-hydroxy-2,6-dimethylbenzyl)dithiol terephthalate, 1,3,5-tris-(3,5-di-tert.-butyl-4-hydroxybenzyl) isocyanurate, 1,3,5-tris-(4-tert.-butyl-3-hydroxy-2,6-dimethylbenzyl) isocyanurate, dioctadecyl 3,5-di-tert.-butyl-4-hydroxybenzyl-phosphonate and monoethyl 3,5-di-tert.-butyl-4-hydroxybenzyl-phosphonate, calcium salt.

1.6. Acylaminophenols: 4-hydroxy-lauric acid anilide, 4-hydroxy-stearic acid anilide, 2,4-bis-octylmercapto-6-(3,5-di-tert.-butyl-4-hydroxyanilino)-s-triazine and octyl N-(3,5-di-tert.-butyl-4-hydroxyphenyl)-carbamate.

1.7. Esters of β-(3,5-di-tert.-butyl-4-hydroxyphenyl)-propionic acia with monohydric or polyhydric alcohols, for example with methanol, diethylene glycol, octadecanol, triethylene glycol, 1,6-hexanediol, pentaerythritol, neopentylglycol, tris-hydroxyethyl isocyanurate, thiodiethylene glycol or di-hydroxyethyl-oxalic acid diamide.

1.8. Esters of β-(5-tert.-butyl-4-hydroxy-3-methylphenyl)propionic acid with monohydric or polyhydric alcohols, for example with methanol, diethylene glycol, octadecanol, triethylene glycol, 1,6-hexanediol, pentaerythritol, neopentylglycol, tris-hydroxyethyl isocyanurate, thiodiethylene glycol or di-hydroxyethyl-oxalic acid diamide.

1.9. Amides of β-(3,5-di-tert.-butyl-4-hydroxyphenyl)-propionic acid, for example N,N'-di-(3,5-di-tert.-butyl-4-hydroxyphenylpropionyl)-hexamethylenediamine, N,N'-di-(3,5-di-tert.-butyl-4-hydroxyphenylpropionyl)-trimethylenediamine and N,N'-di-(3,5-di-tert.-butyl-4-hydroxyphenylpropionyl)hydrazine.

2. UV absorbers and light stabilisers 2.1. 2-(2'-Hydroxyphenyl)-benzotriazoles, for example the 5'-methyl, 3',5'-di-tert.-butyl, 5'-tert.-butyl, 5'-(1,1,3,3-tetramethylbutyl), 5-chloro-3',5'-di-tert.-butyl, 5-chloro-3'-tert.-butyl-5'-methyl, 3'-sec.-butyl-5'-tert.-butyl, 4'-octoxy, 3',5'-di-tert.-amyl and 3',5'-bis-(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tert.-butyl-phenyl salicylate, phenyl salicylate, octylphenyl salicylate, dibenzoylresorcinol, bis-(4-tert.-butylbenzoyl)-resorcinol, benzoylresorcinol, 2,4-di-tert.-butylphenyl 3,5-di-tert.-butyl-4-hydroxybenzoate and hexadecyl 3,5-di-tert.-butyl-4-hydroxybenzoate.

2.4. Acrylates, for example ethyl and isooctyl α-cyano-β,β-diphenylacrylate, methyl α-carbomethoxy-cinnamate, methyl and butyl α-cyano-β-methyl-p-methoxy-cinnamate, methyl α-carbomethoxy-p-methoxy-cinnamate and N-(β-carbomethoxy-β-cyanovinyl)-2-methyl-indoline.

2.5. Nickel compounds, for example nickel complexes of 2,2'-thio-bis-[4-(1,1,3,3-tetramethylbutyl)-phenol], such as the 1:1 or 1:2 complex, with or without additional ligands, such as n-butylamine, triethanolamine or N-cyclohexyl-diethanolamine, nickel dibutyldithiocarbamate, nickel salts of monoalkyl esters of 4-hydroxy-3,5-di-tert.-butylbenzyl-phosphonate, such as the methyl or ethyl ester, nickel complexes of ketoximes, such as 2-hydroxy-4-methyl-phenyl undecyl ketone oxime, and nickel complexes of 1-phenyl-4-lauroyl-5-hydroxypyrazole, with or without additional ligands.

2.6. Sterically hindered amines, for example bis-(2,2,6,6-tetramethylpiperidyl) sebacate, bis-(1,2,2,6,6-pentamethylpiperidyl) sebacate, bis(1,2,2,6,6-pentamethylpiperidyl) n-butyl-3,5-di-tert.-butyl-4-hydroxybenzyl-malonate, the condensation product of 1-hydroxyethyl-2,2,6,6-tetramethyl-4-hydroxypiperidine and succinic acid, the condensation product of N,N'-(2,2,6,6-tetramethyl-4-piperidyl)-hexamethylenediamine and 4-tert.-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl)-1,2,3,4-butanetetracarboxylic acid and 1,1'-(1,2-ethanediyl)-bis-(3,3,5,5-tetramethyl-piperazinone).

2.7. Oxalic acid diamides, for example 4,4'-di-octyloxy-yoxanilide, 2,2'-di-octyloxy-5,5'-di-tert.-butyl-oxanilide, 2,2'-di-dodecyloxy-5,5'-di-tert.-butyl-oxanilide, 2- ethoxy-2'-ethyl-oxanilide, N,N'-bis-(3-dimethylaminopropyl)-oxalamide, 2-ethoxy-5-tert.-butyl-2'-ethyloxanilide and its mixture with 2-ethoxy-2'-ethyl-5,4'-di-tert.-butyl-oxanilide, and mixtures of ortho- and para-methoxy- and of o- and p-ethoxy-di-substituted oxanilides.

3. Metal deactivators, for example N,N'-diphenyloxalic acid diamide, N-salicylal-N'-salicyloylhydrazine, N,N'-bis-salicyloylhydrazine, N,N'-bis-(3,5-di-tert.-butyl-4-hydroxyphenylpropionyl)-hydrazine, 3-salicyloylamino-1,2,4-triazole and bis-benzylideneoxalic acid dihydrazide.

4. Phosphites and phosphonites, for example triphenyl phosphite, diphenyl alkyl phosphites, phenyl dialkyl phosphites, tri-(nonylphenyl) phosphite, trilauryl phosphite, trioctadecyl phosphite, distearyl pentaerythritol diphosphite, tris-(2,4-di-tert.-butylphenyl) phosphite, diisodecyl pentaerythritol diphosphite, di-(2,4-tert.-butylphenyl) pentaerythritol diphosphite, tristearyl sorbitol triphosphite and tetrakis-(2,4-di-tert.-butylphenyl)-4,4'-biphenylene diphosphonite.

5. Compounds which destroy peroxide, for example esters of β-thio-dipropionic acid, for example the lauryl, stearyl, myristyl or tridecyl ester, mercaptobenzimidazole, the zinc salt of 2-mercaptobenzimidazole, zinc dibutyl-dithiocarbamate, dioctadecyl disulfide and pentaerythritol tetrakis-(β-dodecylmercapto)-propionate.

6. Polyamide stabilisers, for example copper salts in combination with iodides and/or phosphorus compounds and salts of divalent manganese.

7. Basic Co stabilisers, for example melamine, polyvinylpyrrolidone, dicyanodiamide, triallyl cyanurate, urea derivatives, hydrazine derivatives, amines, polyamides, polyurethanes and alkali metal and alkaline earth metal salts of higher fatty acids, for example Ca stearate, Zn stearate, Mg stearate, Na ricinoleate, K palmitate, antimony pyrocatecholate or tin pyrocatecholate.

8. Nucleating agents, for example 4-tert.-butylbenzoic acid, adipic acid and diphenylacetic acid.

9. Fillers and reinforcing agents, for example calcium carbonate, silicates, glass fibres, asbestos, talc, kaolin, mica, barium sulfate, metal oxides and hydroxides, carbon black and graphite.

10. Other additives, for example plasticisers, lubricants, emulsifiers, pigments, fluorescent brighteners, flameproofing agents, antistatics and blowing agents.

11. Aminic antioxidants: N,N'-di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methylpentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec.-butyl-p-phenylenediamine, diphenylamine, 4-isopropoxy-diphenylamine, N-phenyl-1-naphthylamine, N-phenyl-2-naphthylamine, octylated diphenylamine, 4-n-butylaminophenol, 4-butyrylamino-phenol, 4-nonanoylamino-phenol, 4-dodecanoylamino-phenol, 4-octadecanoylamino-phenol, di-(4-methoxy-phenyl)-amine, 2,6-di-tert.-butyl-4-dimethylaminomethyl-phenol, 2,4'-diamino-diphenylmethane, 4,4'-diaminodiphenylmethane, N,N,N',N'-tetramethyl-4,4'-diaminodiphenylmethane, 1,2-di-(phenylamino)-ethane, 1,2-di-[(2-methylphenyl)-amino]-ethane, 1,3-di-(phenylamino)-propane, (otolyl)-biguanide and di-[4-(1',3'-dimethyl-butyl)-phenyl]amine.

12. Metal passivators: for copper, for example: benzotriazole, tetrahydrobenzotriazole, 2-mercaptobenzothiazole, 2,5-dimercaptothiadiazole, salicylidenepropylenediamine and salts of salicylaminoguanidine.

13. Rust inhibitors:

(a) Organic acids and their esters, metal salts and anhydrides, for example: N-oleoyl-sarcosine, sorbitan monooleate, lead naphthenate, dodecenylsuccinic anhydride, alkenylsuccinic acid half-esters and 4-nonylphenoxy-acetic acid.

(b) Nitrogen-containing compounds, for example:

I. Primary, secondary or tertiary aliphatic or cycloaliphatic amines and amine salts of organic and inorganic acids, for example oil-soluble alkylammonium carboxylates.

II. Heterocyclic compounds, for example: substituted imidazolines and oxazolines.

(c) Phosphorus-containing compounds, for example: amine salts of phosphoric acid partial esters.

(d) Sulfur-containing compounds, for example: barium dinonyl-naphthalene-sulfonates and calcium petroleum-sulfonates.

14. Agents which improve the viscosity index: Polymethacrylates, vinylpyrrolidone/methacrylate copolymers, polybutenes, olefine copolymers and styrene/acrylate copolymers.

15. Agents which reduce the pour point: polymethacrylate and alkylated naphthalene derivatives.

16. Dispersants/surfactants: polybutenylsuccinimides, polybutenylphosphonic acid derivatives and basic magnesium, calcium and barium sulfonates and phenolates.

17. Wear protection additives: compounds containing sulfur and/or phosphorus and/or halogen, such as sulfurised vegetable oils, zinc dialkyl dithiophosphates, tritolyl phosphate, chlorinated paraffins and alkyl and aryl disulfides.

Preparation Examples

EXAMPLE 1

10.4 g of 2-tert.-butylphenol, 20.5 g of 2-ethylhexylmercaptan, 10 ml of dimethylformamide, 0.7 ml of dibutylamine and 8.1 g of paraformaldehyde are heated at 120° C. under nitrogen for 25 hours. After the solution has been cooled to room temperature, it is diluted with toluene and washed neutral with 2N hydrochloric acid and water in the customary manner. Concentration of the residue on a Rotavap gives a good yield of 2,4-bis-(2-ethylhexylthiomethyl)-6-tert.-butyl-phenol, which is further purified by column chromatography on silica gel; colourless oil, calculated S 13.74%, found S 13.56% (characteristic data in Table 2).

EXAMPLE 2

60.1 g of 2-tert.-butylphenol, 170 g of dodecylmercaptan, 60 ml of dimethylformamide, 3.1 g of dibutylamine and 24.2 g of paraformaldehyde are heated at 130° C. under nitrogen for 24 hours. Working up as under Example 1 gives 2,4-bis-dodecylthiomethyl-6-tert.-butylphenol; colourless oil, calculated S 11.07%, found S 11.03% (characteristic data in Table 2).

EXAMPLE 3

The compound described under Example 2 is also obtained by heating 26.4 g of bis-2,4-dimethylaminomethyl-6-tert.-butylphenol, 40.5 g of dodecylmercaptan and 200 ml of dimethylformamide at 140° C. for 20 hours. Calculated S 11.07%, found S 11.30% (characteristic data in Table 2).

EXAMPLE 4

The procedure described under Example 3 is repeated, except that 43.7 g of 2-ethylhexyl 2-mercaptopropionate are used in place of dodecylmercaptan, affording 2,4-bis-[2-(2-ethylhexyloxycarbonyl)ethylthiomethyl]-6-tert.-butylphenol; colourless oil, calculated S 10.50%, found S 10.52% (characteristic data in Table 2).

The compounds listed in the following Table 1 are obtained by a process analogous to that of Example 1 or 3.

TABLE 1

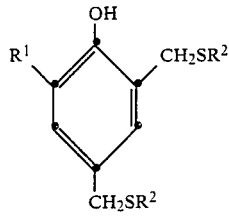

| No. | $R^1$ | $R^2$ | Process[1] | Characterisation | Analysis (%) calculated % | found % |
|---|---|---|---|---|---|---|
| 5[2] | —C(CH$_3$)$_3$ | —(CH$_2$)$_7$—CH$_3$ | b | Oil | 13,73 | 13,42 |
| 6[2] | —C$_6$H$_5$ | —CH$_2$—COO—CH$_2$—CH(C$_2$H$_5$)—(CH$_2$)$_3$—CH$_3$ | a | Oil | 10,64 | 10,86 |
| 7[2] | —C(CH$_3$)$_3$ | —CH$_2$—COO—CH$_2$—CH(C$_2$H$_5$)—(CH$_2$)$_3$—CH$_3$ | b | Oil | 11,00 | 10,86 |
| 8[2] | —C(CH$_3$)$_3$ | 1:1 mixture of —C(CH$_3$)$_2$—CH$_2$—C(CH$_3$)$_2$—CH$_2$—C(CH$_3$)$_3$ and —C(CH$_3$)(CH$_2$—C(CH$_3$)$_3$)$_2$ | b | yellowish, clear oil | 11,07 | 11,03 |
| 9[2] | —C(CH$_3$)$_3$ | t-C$_8$H$_{17}$— | a | m.p. 61° | 13,74 | 13,63 |
| 10[2] | —C(CH$_3$)$_3$ | t-C$_9$H$_{19}$— | b | m.p. 50° | 12,96 | 13,57 |
| 11[2] | —C(CH$_3$)$_3$ | —CH$_2$CH$_2$OH | b | oil | 19,40 | 19,20 |
| 12[2] | —C(CH$_3$)$_3$ | —CH$_2$—CH(OH)CH$_2$OH | b | oil | 16,42 | 16,05 |
| 13[2] | —C(CH$_3$)$_3$ | —CH$_2$CH$_2$O—C(=O)—(CH$_2$)$_2$—[3,5-di-t-butyl-4-hydroxyphenyl] | a | resin | 7,53 | 7,33 |

[1] a: Process according to Example 1
b: Process according to Example 3
[2] Characteristic data in Table 2

Typical signals in the $^1$H-NMR spectrum of the compounds described

The methylene protons of the aryl-CH$_2$-S groupings absorb as 2 singlets in the $^1$H-NMR spectrum (CDCl$_3$). The chemical shifts are summarised in Table 2 (standard: TMS).

TABLE 2

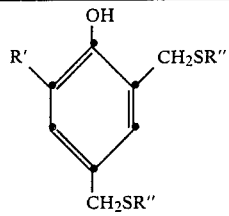

| Example No. | R′ | R″ | Aryl—CH$_2$—S— signal ortho-CH$_2$(ppm) | para-CH$_2$(ppm) | Type of instrument |
|---|---|---|---|---|---|
| 1 | —C(CH$_3$)$_3$ | —CH$_2$—CH(C$_2$H$_5$)—(CH$_2$)$_3$—CH$_3$ | 3,79 | 3,60 | b |
| 2/3 | —C(CH$_3$)$_3$ | —(CH$_2$)$_{11}$—CH$_3$ | 3,76 | 3,60 | b |
| 4 | —C(CH$_3$)$_3$ | —(CH$_2$)$_2$—COO—CH$_2$—CH(C$_2$H$_5$)—(CH$_2$)$_3$—CH$_3$ | 3,77 | 3,60 | a |
| 5 | —C(CH$_3$)$_3$ | —(CH$_2$)$_7$—CH$_3$ | 3,78 | 3,62 | c |
| 6 | —C(CH$_3$)$_3$ | —CH$_2$—COO—CH$_2$—CH(C$_2$H$_5$)—(CH$_2$)$_3$—CH$_3$ | 3,86 | 3,73 | b |

TABLE 2-continued

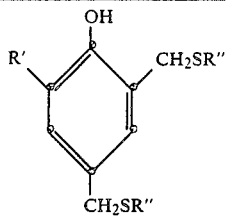

| Example No. | R' | R" | Aryl—CH₂—S— signal ortho-CH₂(ppm) | para-CH₂(ppm) | Type of instrument |
|---|---|---|---|---|---|
| 7 | —C₆H₅ | —CH₂—COO—CH₂—CH(C₂H₅)—(CH₂)₃—CH₃ | 3,94 | 3,80 | b |
| 8 | —C(CH₃)₃ | Mixture of —C(CH₃)₂—CH₂—C(CH₃)₂—CH₂—C(CH₃)₃ and —C(CH₃)(CH₂—C(CH₃)₃)₂ | 3,77 and 3,70 | 3,61 and 3,54 | b |
| 9 | —C(CH₃)₃ | t-C₈H₁₇— | 3,80 | 3,65 | c |
| 10 | —C(CH₃)₃ | t-C₉H₁₉— | 3,84 | 3,66 | c |
| 11 | —C(CH₃)₃ | —CH₂CH₂OH | 3,85 | 3,66 | c |
| 12 | —C(CH₃)₃ | —CH₂CH(OH)CH₂OH | 3,81 | 3,64 | c |
| 13 | —C(CH₃)₃ | 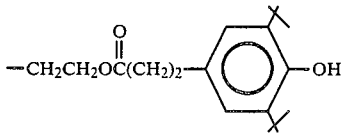 | 3,82 | 3,67 | c | a: 60 MHz
b: 250 MHz
c: 100 MHz

USE EXAMPLE

TOST-TEST, oxidation characteristics of mineral oil Mobil 150 SS4 (ASTM D934/DIN 51587/IP 157)

The oil to be tested is warmed at 95° C. for 500 hours in the presence of water, oxygen, an iron/copper catalyst and the particular stabiliser. Thereafter, the acid value (in mg of KOH consumed per g of test oil) and the sludge (in mg of residue per batch) are determined. The results are summarised in Table 3. The concentration of the stabiliser is 0.25% by weight, based on the oil.

TABLE 3

| Stabiliser | Acid value (mg of KOH/g) | Sludge (mg) |
|---|---|---|
| Example 2 | 0.21 | 3.9 |
| Example 5 | 0.22 | 1.0 |

What is claimed is:

1. A compound of the formula I

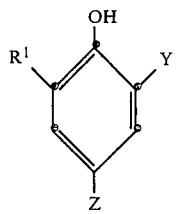

in which R¹ is C₂-C₂₀-alkyl, C₃-C₂₀-alkenylmethyl, C₃-C₂₀-alkinylmethyl, C₅-C₁₂-cycloalkyl, phenyl, 1- or 2-naphthyl, C₇-C₁₄-alkaryl or C₇-C₁₄-aralkyl, Y is —CH₂—S—R² and Z is —CH₂—S—R³, or in which Y and/or Z is a radical

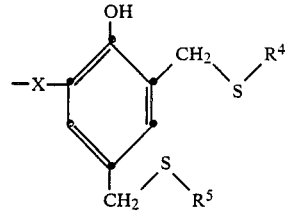

in which R², R³, R⁴ and R⁵ independently of one another are C₁-C₂₀-alkyl, C₂-C₂₀-alkyl which is substituted by a phenyl radical and/or one or two hydroxyl groups, C₃-C₂₀-alkenylmethyl, C₃-C₂₀-alkinylmethyl, C₅-C₁₂-cycloalkyl, phenyl, 1- or 2-naphthyl, C₇-C₁₄-alkaryl, C₇-C₁₄-aralkyl, C₅-C₇-cycloalkyl which is substituted by hydroxyl in the 2-position or radicals of the formula —C(R⁶R⁷)—(CHR⁸)ₘ—W, —(CH₂)₂—OCO—R¹⁵ or

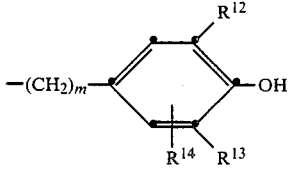

in which m is 0, 1 or 2, R⁶, R⁷ and R⁸ independently of one another are hydrogen or C₁-C₆-alkyl, W is a radical —COR⁹, —CN, —COOR¹⁰ or —CON(R¹⁰R¹¹), in which R⁹ is hydrogen, C₁-C₂₀-alkyl, phenyl, 1- or 2-naphthyl, C₅-C₁₂-cycloalkyl, C₇-C₁₄-aralkyl or C₇-C₁₄-alkaryl and in which R¹⁰ and R¹¹ independently of one another have the meanings of R⁹, or are additionally C₂-C₂₀-alkyl which is substituted by a hydroxyl or cyano group, or are C₃-C₂₀-alkyl which is interrupted by one to five —O—, —S—, —N(CH₃)— or —N(C₂H-

5)— and is unsubstituted or substituted by a hydroxyl group, it being necessary for the several heteroatoms which may occur to be separated by at least one methylene group, in which $R^{10}$ or $R^{11}$ is $C_2$-$C_{12}$-alkenyl, $C_2$-$C_{12}$-alkinyl, phenyl which is substituted by one or two —$NO_2$, —Cl, —Br, —$OCH_3$ or —$COOR^{18}$, or a group

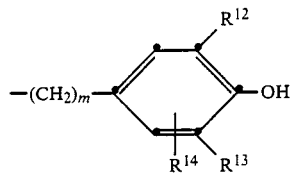

in which $R^{12}$, $R^{13}$ and $R^{14}$ independently of one another are hydrogen, $C_1$-$C_{20}$-alkyl, cyclohexyl or phenyl, in which $R^{15}$ is $C_1$-$C_{20}$-alkyl, $C_5$-$C_{12}$-cycloalkyl, $C_7$-$C_{14}$-aralkyl, $C_7$-$C_{14}$-alkaryl, phenyl, 1- or 2-naphthyl or a radical

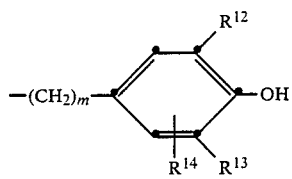

in which X is —$C(R^{16}R^{17})$—, —S— or —S—S—, in which $R^{16}$ and $R^{17}$ independently of one another are hydrogen, $C_1$-$C_6$-alkyl, cyclohexyl or phenyl, and in which, finally, $R^{18}$ is $C_1$-$C_6$-alkyl, cyclohexyl, phenyl, benzyl or tolyl.

2. A compound of the formula I according to claim 1, in which $R^1$ is branched $C_3$-$C_{12}$-alkyl.

3. A compound of the formula I according to claim 1, in which $R^1$ is tert.-butyl.

4. A compound of the formula I according to claim 1, in which Y is —$CH_2$—S—$R^2$ and Z is —$CH_2S$—$R^3$.

5. A compound of the formula I according to claim 1, in which $R^1$ is branched $C_3$-$C_{12}$-alkyl, $C_5$-$C_9$-cycloalkyl, phenyl or $C_7$-$C_9$-aralkyl, in which $R^2$ and $R^3$ independently of one another are $C_4$-$C_{14}$-alkyl, $C_2$-$C_{14}$-alkyl which is substituted by a phenyl and/or one or two hydroxyl groups, allyl, propargyl, $C_5$-$C_9$-cycloalkyl, 2-hydroxycyclohexyl, phenyl, or $C_7$-$C_9$-aralkyl, or are a radical —$C(R^6R^7)$—$(CHR^8)_m$—W, —$(CH_2)_2$—OCO—$R^{15}$ or

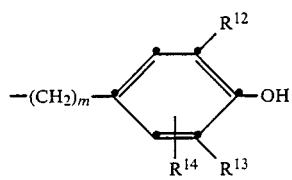

in which m is 0, 1 or 2, and in which $R^6$, $R^7$ and $R^8$ independently of one another are hydrogen or methyl, W is —$COOR^{10}$ or —$CON(R^{10}R^{11})$, in which $R^{10}$ and $R^{11}$ independently of one another are hydrogen, $C_1$-$C_{12}$-alkyl, phenyl, $C_5$-$C_9$-cycloalkyl, $C_7$-$C_9$-aralkyl, 2-hydroxyethyl, 2-cyanoethyl, or $C_3$-$C_{12}$-alkyl which is interrupted by one to three —O— and is unsubstituted or substituted by a hydroxyl group, it being necessary for several oxygen atoms which may occur to be separated by at least one methylene group, in which $R^{10}$ and $R^{11}$ are allyl, propargyl, phenyl which is substituted by a —Cl, —$COOCH_3$ or —$OCH_3$, or a radical

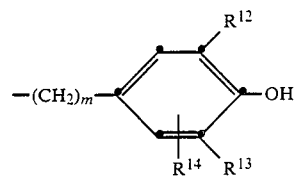

in which $R^{12}$, $R^{13}$ and $R^{14}$ independently of one another are hydrogen or $C_1$-$C_{12}$-alkyl, and in which $R^{15}$ is $C_1$-$C_{12}$-alkyl, $C_5$-$C_9$-cycloalkyl, $C_7$-$C_9$-aralkyl, phenyl or a radical

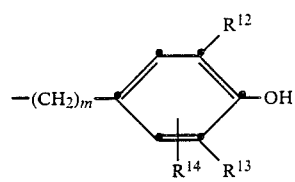

6. A compound of the formula I according to claim 1, in which $R^1$ is tert.-butyl, cyclohexyl, phenyl or benzyl, and in which $R^2$ and $R^3$ independently of one another are $C_4$-$C_{14}$-alkyl, 2-hydroxyethyl, 2,3-dihydroxypropyl, 1-phenyl-2-hydroxyethyl, cyclohexyl, phenyl or benzyl.

7. A compound of the formula I according to claim 1, in which $R^1$ is tert.-butyl, cyclohexyl, phenyl or benzyl, in which $R^2$ and $R^3$ are radicals of the formula —$(CH_2)_{m+1}$—W, in which W is —$COOR^{10}$ or —$CON(R^{10}R^{11})$, and in which $R^{10}$ and $R^{11}$ independently of one another denote hydrogen, $C_1$-$C_{12}$-alkyl, phenyl, cyclohexyl, benzyl, 2-hydroxyethyl, 2-hydroxypropyl, 5-hydroxy-3-oxapentyl or 3-oxabutyl, or are a radical

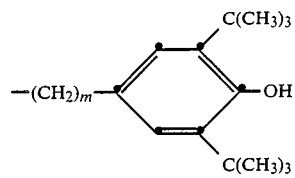

8. A compound of the formula I according to claim 1, in which $R^1$ is tert.-butyl and $R^2$ and $R^3$ are each 2-ethylhexyl, t-octyl, n-dodecyl or t-dodecyl radicals.

9. The compound of the formula I according to claim 8, in which $R^2$ and $R^3$ are n-octyl.

10. The compound of the formula I according to claim 8, in which $R^2$ and $R^3$ are n-dodecyl.

11. The compound of formula I according to claim 1 in which $R^2$ and $R^2$ are 2-ethylhexyl.

12. A stabilized composition which comprises
(a) a polymer, a mineral oil lubricant or a synthetic lubricant, and
(b) an effective stabilizing amount of at least one compound of formula I according to claim 1.

13. A stabilized composition which comprises
(a) an elastomer, a mineral oil lubricant or a synthetic lubricant, and
(b) an effective stabilizing amount of a compound of formula I according to claim 6.

14. A compound of formula I
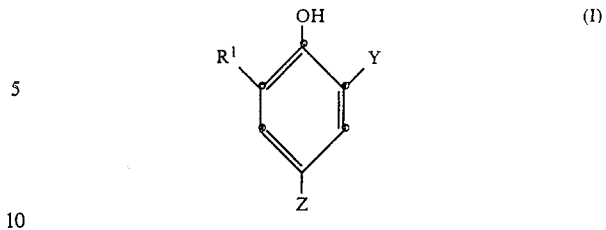
in which $R^1$ is $C_2$–$C_{20}$-alkyl, $C_3$–$C_{20}$-alkenylmethyl, $C_3$–$C_{20}$-alkynylmethyl, $C_5$–$C_{12}$-cycloalkyl, phenyl, 1-naphthyl, 2-naphthyl, $C_7$–$C_{14}$-alkaryl or $C_7$–$C_{14}$-aralkyl, Y is —$CH_2$—S—$R^2$ and Z is —$CH_2$—S—$R^3$, where $R^2$ and $R^3$ are independently $C_1$–$C_{20}$-alkyl.
* * * * *